United States Patent [19]
Fahrenkrug

[11] Patent Number: 4,891,258
[45] Date of Patent: Jan. 2, 1990

[54] STRETCHABLE ABSORBENT COMPOSITE

[75] Inventor: Anne M. Fahrenkrug, Appleton, Wis.

[73] Assignee: Kimberly-Clark Corporation, Neenah, Wis.

[21] Appl. No.: 137,291

[22] Filed: Dec. 22, 1987

[51] Int. Cl.[4] ............................................. B32B 3/10
[52] U.S. Cl. .................................... 428/138; 428/131; 428/152; 428/178; 428/184; 428/284; 428/913
[58] Field of Search ............... 428/131, 138, 184, 185, 428/186, 152, 284, 287, 913, 178; 156/163, 164

[56] References Cited

U.S. PATENT DOCUMENTS

| | | | |
|---|---|---|---|
| 3,695,985 | 10/1972 | Brock et al. | 161/129 |
| 3,770,562 | 11/1973 | Newman | 161/156 |
| 3,793,133 | 2/1974 | Beaudoin et al. | 161/148 |
| 4,013,816 | 3/1977 | Sabee et al. | 428/288 |
| 4,041,203 | 8/1977 | Brock et al. | 428/157 |
| 4,050,462 | 9/1977 | Woon et al. | 604/385.2 |
| 4,275,105 | 6/1981 | Boyd et al. | 428/198 |
| 4,287,251 | 9/1981 | King et al. | 428/198 |
| 4,411,660 | 10/1983 | Dawn et al. | 604/396 |
| 4,606,964 | 8/1986 | Wideman | 428/152 |
| 4,650,481 | 3/1987 | O'Connor et al. | 604/380 |
| 4,655,760 | 4/1987 | Morman et al. | 604/385 |
| 4,720,415 | 1/1988 | Wielen et al. | 428/152 |

FOREIGN PATENT DOCUMENTS 8603964 7/1986 PCT Int'l Appl. .

Primary Examiner—James J. Bell
Attorney, Agent, or Firm—John L. Chiatalas

[57] ABSTRACT

The stretchable composite comprises a liquid-pervious layer, liquid-impervious layer, an absorbent layer, and a stretchable layer. The stretchable layer is stretch-bonded to the other layers and, upon relaxing the stretched layer, a plurality of rugosities are formed in the liquid-pervious layer, liquid-impervious layer, and absorbent layer. A method is provided for making the composite.

30 Claims, 7 Drawing Sheets

– 1 –

STRETCHABLE ABSORBENT COMPOSITE

BACKGROUND OF THE INVENTION

This invention pertains to absorbent materials or structures, and more particularly to a stretchable absorbent composite for absorbing and retaining liquids.

Various types of absorbent structures presently exist, and include single and multilayer structures comprising materials such as cellulosic fluff, synthetic fibers, blends of fluff and synthetic fibers, and these various structures with superabsorbent materials. Some of the important characteristics or features these structures should preferably possess are rapid transfer rates and absorbent rates, high capacity, high retention, dry flexibility and wet flexibility, dry integrity and wet integrity, and low flowback properties.

One of the recurring problems with current absorbent structures is that they sacrifice one or more of the above characteristics or features in order to possess or increase the effect of others. For example, absorbency generally can be maximized by a combination of fluff and superabsorbent material, but one of the problems with this combination is its integrity. When dry, the fluff tends to be redistributed by the movement or activities of the wearer, thereby decreasing its absorbency in the areas of maximum wetting. Similarly, after wetting, the combination tends to gather or cluster into separate masses or lumps of wetted fluff, which are very uncomfortable and visibly embarrassing to the wearer.

One solution to the above problem is to provide a mechanism that maintains the integrity of the absorbent material, such as introducing amounts of binders, synthetic fibers or the like. Though this may increase dry and wet integrity, it generally causes a decrease in absorbency and in flexibility, which to the wearer translates into a relatively stiff-feeling material or structure.

SUMMARY OF THE INVENTION

In one form of the invention, there is provided a stretchable absorbent composite for receiving, absorbing and retaining liquids and waste materials comprising a liquid-pervious layer, a liquid-impervious layer, an absorbent layer, and a liquid-pervious stretchable layer between the liquid-pervious layer and liquid-impervious layer. The stretchable layer is stretch-bonded to the other layers and forms a plurality of rugosities in the other layers upon relaxing the stretchable layer.

In another form of the invention, there is provided a method of making a stretchable absorbent composite comprising the steps of providing a liquid-pervious layer, a liquid-pervious stretchable layer, an absorbent layer and a liquid-impervious layer; stretching the stretchable layer; bonding the layers together with the stretchable layer in the stretched state; releasing the bonded layers; and forming a plurality of rugosities in the liquid-pervious layer, the absorbent layer and the liquid-impervious layer upon release of the stretchable layer.

BRIEF DESCRIPTION OF THE DRAWINGS

The above-mentioned and other features and objects of this invention, and the manner of attaining them, will become more apparent, and the invention itself will be better understood by reference to the following description of an embodiment of the invention taken in conjunction with the accompanying drawings, wherein.

DEFINITIONS

As used herein and in the claims, the term "elastic," "elastic characteristics," "stretch" and "stretchable" are used interchangeably to define a material or composite which can be elongated by at least 25% of its relaxed length, i.e., elongated to at least 1¼ times its relaxed length (an elongation of 25%), and which will recover upon release of the applied force at least 10% of its elongation. According to this definition, upon release of the applied force at 25% elongation, the material or composite must recover to at least about a 15% elongation. For example, a material or composite is deemed to be "elastic" if a sample length of 100 centimeters can be elongated to a length of at least 125 centimeters, and upon release of the applied force recovers to a length of not more than about 115 centimeters. Many elastic or stretchable materials or composites can be elongated by more than 25% of their relaxed length, and many of these will recover to, or close to, their original relaxed length upon release of the applied force. This latter class of materials is generally preferred for purposes of the present invention. These materials can include not only webs of elastic or stretchable films, such as cast or blown films, but also nonwoven fibrous elastic webs such as meltblown elastomeric fibrous nonwoven webs.

The term "bonding" can mean the joining, adhering, connecting, attaching or the like of two layers or composites, either directly or indirectly together. For example, three layers are directly bonded together if the bond is effective throughout the three layers. These three layers are also said to be bonded if, for example, the outermost two layers are directly bonded along their peripheries so as to capture or sandwich the middle layer therebetween.

The term "transfer layer" refers to a layer of material that primarily directs fluid flow in the Z-direction, which is the direction through the thickness of the layer.

The term "wicking layer" refers to a layer that primarily directs liquid flow in multiple directions in the X-Y plane, which is the plane defined by the length and width of the layer.

DETAILED DESCRIPTION

Figure 1:
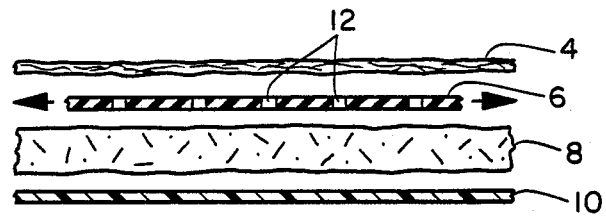
FIG. 1 illustrates one embodiment of the composite before the layers are joined together.
Figure 2:
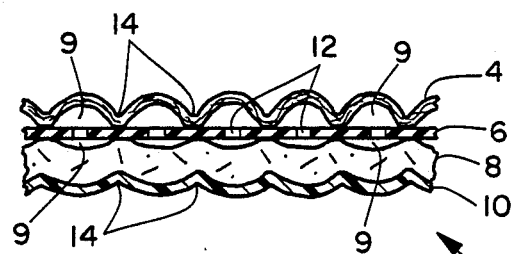
FIG. 2 is the embodiment of FIG. 1 after the layers have been joined together.

Referring to FIGS. 1 and 2, one embodiment of the stretchable absorbent composite 2 comprises liquid-permeable bodyside liner 4, liquid-permeable stretchable or elastomeric layer 6, absorbent medium 8 and liquid-impermeable outer cover 10. In this particular embodiment, elastomeric layer 6 is made permeable by a plurality of apertures 12 disposed therein.

Figure 5:
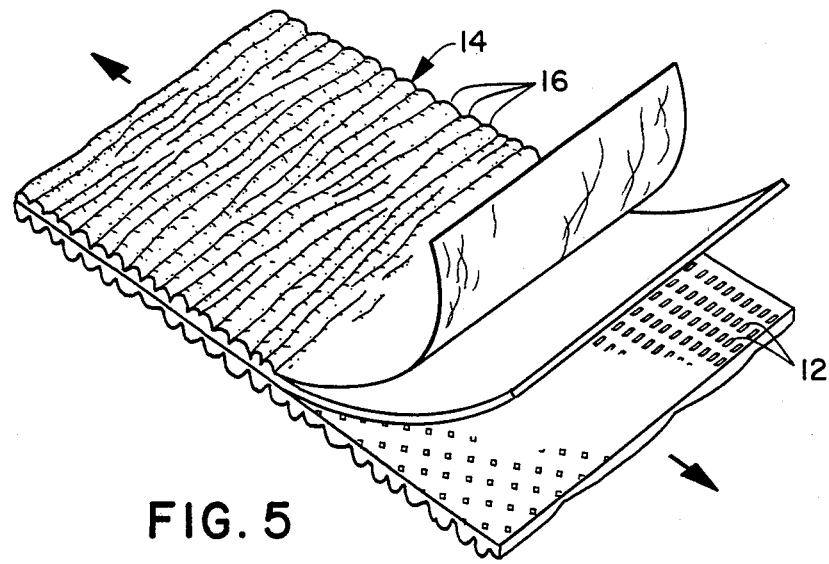
FIG. 5 is a perspective view of the embodiment in FIG. 4 with the top two layers peeled back in order to view the apertures in one of the layers.
Figure 5A:
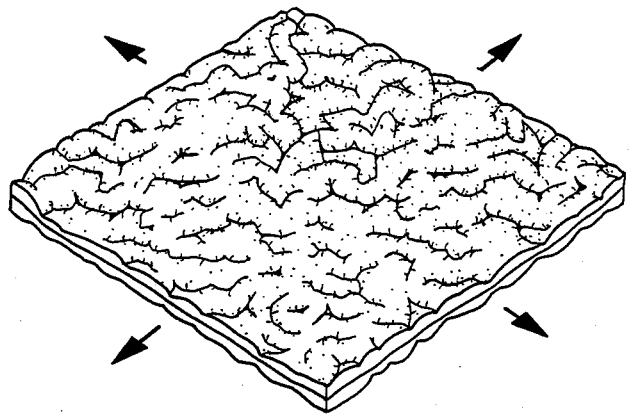
FIG. 5A is a multi-directional stretchable absorbent composite.
Figure 16:
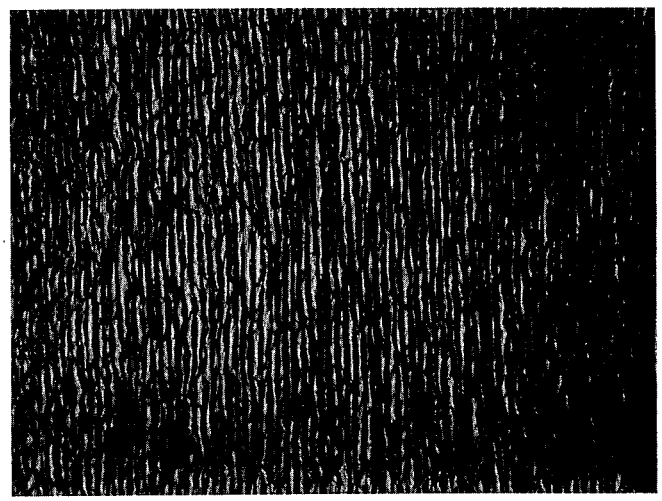
FIG. 16 is similar to FIG. 15 of the other side.
Figure 17:
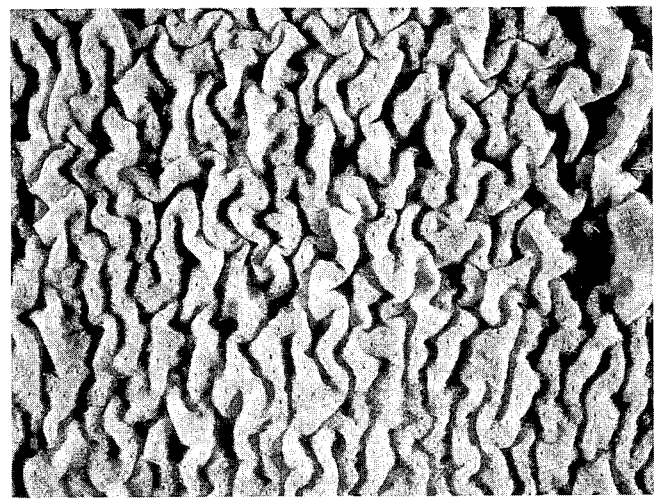
FIG. 17 is a photographic plan view of one side of a multi-stretched composite.
Figure 18:
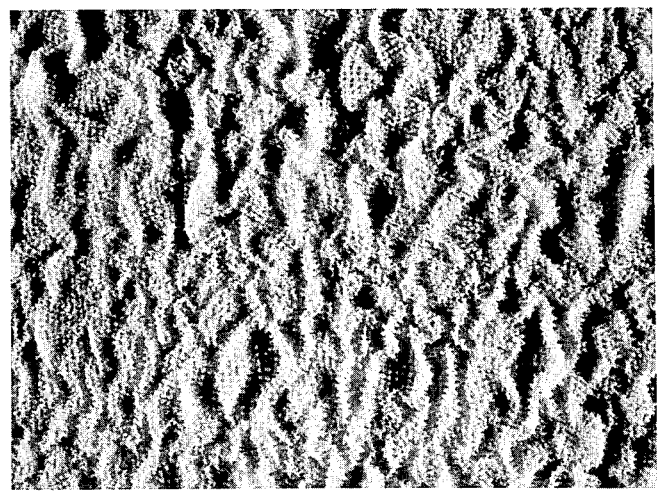
FIG. 18 is similar to FIG. 17 of the other side.

FIG. 1 illustrates composite 2 with the layers separated and the stretchable or elastomeric layer 6 in its relaxed, unstretched condition. In the manufacture of composite 2, which will be described in greater detail below, elastomeric layer 6 is stretched to a desired elongation, and then liner 4, elastomeric layer 6, absorbent assembly 8 and cover 10 are bonded together. After the bonding, composite 2 is relaxed so that elastomeric layer 6 will recover from its stretched state. In doing so, liner 4, absorbent medium 8 and outer cover 10 are gathered, as illustrated in FIG. 2, to form a plurality of rugosities 14 and a plurality of air pockets 9 on either side of elastomeric layer 6 within or inside composite 2. Naturally, rugosities 14 inherently form or create air spaces between one another. When elastomeric layer 6 is elongated in a single direction, such as the machine direction indicated by arrows in FIG. 5, the rows 16 (FIGS. 5 and 15, 16) of rugosities 14, and air pockets 9, are generally perpendicular to the direction, i.e., machine direction of elongation of elastomeric layer 6. If elastomeric layer 6 is multi-directionally elongated, for example, in the X- and Y- directions, then the finished stretchable absorbent composite 2 has a quilted-like or wormy pattern, as illustrated in FIGS. 5A and 17, 18.

Figure 5B:
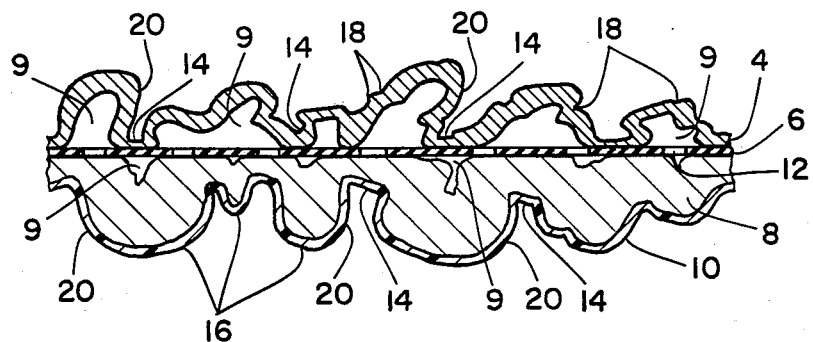
FIG. 5B is an enlarged cross section through FIG. 2.

FIG. 5B illustrates an enlarged cross-sectional view through composite 2 in FIG. 2. Because elastomeric layer 6 is in its relaxed, unstretched condition, liner 4, absorbent 8 and cover 10 have been gathered into a plurality of rows 16 of rugosities 14. Since these layers, i.e., liner 4, absorbent 8 and cover 10, are gathered into rugosities 14, there is a greater amount of surface area per square inch than if the layers were flat or planar. Furthermore, each rugosity 14 has a plurality of smaller or finer wrinkles 18 in its opposite surfaces 20 which extend outwardly relative to elastomeric layer 6. Both rugosities 14 and wrinkles 18 are formed upon relaxing elastomeric layer 6, but they have been differentiated herein to distinguish the larger irregularities of rugosities 14 with the finer irregularities of wrinkles 18. Wrinkles 18 also serve the same purpose as rugosities 14 in providing a larger surface area per square inch of composite 2, as compared to a flat or planar surface.

Since stretchable absorbent composite 2 has a greater surface area per square inch, due to rugosities 14, wrinkles 18, and air pockets 9, it has been discovered that the functions of the particular layers are surprisingly increased. For example, because liner 4 is gathered into a bulky condition, it has a greater surface area per square inch which results in increased body surface dryness.

Naturally, the greater the surface area of a liquid-receiving layer, the greater amount of liquid the layer can act upon. Similarly, absorbent 8, because of rugosities 14, wrinkles 18, and pockets 9, has an improved capacity per unit area for receiving, absorbing and retaining liquid. Again, because of the increased surface area per square inch of absorbent medium 8, it is better able to handle or manage greater amounts of liquid, as compared to a flat or planar absorbent of the same finished dimensions.

With reference to outer cover 10, the rugosities 14 and wrinkles 18 provide a cover that is quieter during body movement and present a cloth-like appearance.

Liquid permeable bodyside liner 4 can be a nonwoven web or sheet of polyolefin fibers, such as polypropylene, polyester, polyethylene, Rayon, Chisso and the like. Liner 4 can also be a nonwoven web of synthetic or natural fibers or a blend thereof, a plastic film with perforations or an expanded plastic webbing material or a scrim material. Preferably, liner 4 is spunbonded polyethylene or spunbonded polypropylene having a basis weight of about 0.2 to about 1.0 ounces per square yard. More preferably, liner 4 is spunbonded polypropylene having a basis weight of about 0.2 to about 1.0 ounces per square yard. The material of which liner 4 will be made for any specific embodiment or variation can vary depending upon the exact properties or characteristics desired of liner 4. Generally, it is desired that liner 4 be hydrophobic and have high fluid transfer rates, such as a penetration rate of about 0.05 to about 8.0 ml/sec/cm$^2$, and preferably about 0.5 to about 2.5 ml/sec/cm$^2$. Liner 4 also exhibits good hand properties.

A wide variety of materials can be employed as elastomeric layer 6 and include not only webs of elastic films, such as cast or blown films, but also nonwoven fibrous elastic webs such as, for example, meltblown or spunbonded elastomeric fibrous nonwoven webs. Elastomers may be incorporated into any one of the layers, for example, the meltblown liner, the staple coform absorbent, or the film. Other materials, such as self-adhering elastomeric materials and extrudable elastic films that shrink and become elastic when cooled, are also suitable for use as elastomeric layer 6. A useful material for making elastomeric layer 6, and most preferably for making meltblown elastomeric fibers, is a block copolymer having the general formula A-B-A' wherein A and A' are each a thermoplastic polymer endblock or segment which includes a styrenic moiety and B is an elastomeric polymer midblock such as a conjugated diene or lower alkene. Materials of this general type are disclosed in U.S. Pat. No. 4,333,782, issued June 8, 1980 to H. A. Pieniak. Similar materials are disclosed in U.S. Pat. No. 4,418,123, issued Nov. 29, 1983 to William L. Bunnelle. Commercially available A-B-A' block copolymers having thermoplastic polystyrene endblocks or segments and a saturated or essentially saturated poly(ethylene-butylene) midblock B or segment, sometimes referred to as an S-EB-S polymer, are available under the trade designation KRATON G, for example, Kraton G-1650, Kraton G-1652, Kraton GX-1657 and Kraton G-2740X, from The Shell Chemical Company. Other examples of elastomeric materials for use in the present invention include polyester elastomeric materials such as, for example, those available under the trade designation Hytrel from E. I. DuPont de Nemours and Company; polyurethane elastomeric material such as, for example, those available under the designation Estane from B. F. Goodrich and Company;

and polyamide elastomeric material such as, for example, those available under the trade designation Pebax from the Rilsan Company.

Suitable elastic films, as distinguished from an elastic nonwoven web of elastomeric fibers, may also be utilized in accordance with the invention, for example, elastic film sold under the trade name Polytrope by A. Schulman Corporation of Akron, Ohio.

Elastomeric layer 6 is elongatable or stretchable from about 10% to about 800% of its relaxed length, and has good recovery such as at least about 10%. Elastomeric layer 6 also includes apertures 12 that allow rapid fluid passage or transfer therethrough in the direction toward absorbent medium 8 and eliminates or minimizes liquid flow in the reverse direction. Generally, apertures 12 are provided in any manner resulting in the desired fluid transfer properties or rates. Elastomeric layer 6 can also be liquid-permeable due to inherent pores in the material. For example, a meltblown process provides pores in the meltblown product and the addition of a surfactant, if necessary, makes the meltblown product hydrophilic. A preferred basis weight for elastomeric layer 6 is about 10 grams per square meter to about 200 grams per square meter, and a more preferred basis weight is about 60 grams per square meter to about 150 grams per square meter.

Absorbent medium 8 can be made of any suitable absorbent material, for example, a cellulosic material such as an air-formed batt of wood pulp fibers or a batt of meltblown fibers such as polypropylene, polyethylene, polyester and the like. Absorbent medium 8 may also be a bonded carded web of synthetic or natural fibers, a composite of meltblown fibers of polypropylene, polyethylene, polyester mixed with a cellulosic material, or a blend of cellulosic material with staple textile fibers such as Rayon and the like. Absorbent medium 8 may also contain superabsorbent materials to increase its absorbent capacity. Examples of suitable superabsorbent materials include grafted starch, starch polyacrylic acid grafted methyl cellulose, modified polyvinyl alcohols, polyacrylic acid salts that are crosslinked to form absorbent polymers and the like. Absorbent medium 8 may also include layers of different absorbent structure, such as a meltblown layer of polypropylene and a layer of fluff with a superabsorbent material. Absorbent medium 8 may also be made of a foam-type material or a coform material.

In one preferred embodiment, absorbent medium 8 comprises a blend of 70% by weight polyester and 30% by weight of a binder, such as Chisso, having a basis weight of about 70 grams per square meter and mixed therewith a superabsorbent with a basis weight of about 16 grams per square meter.

In another preferred embodiment, absorbent medium 8 is a blend of 60% by weight fluff pulp and 40% by weight polyethylene, having a basis weight of about 150 grams per square meter, with a superabsorbent having a basis weight of about 16 grams per square meter mixed therewith.

Outer cover 10 can be made of any suitable liquid-impermeable material and can also be made of a liquid-impermeable, air-permeable material. Outer cover 10 is preferably made of a polyethylene or polypropylene film having a thickness between about 0.3 to about 1.5 mils and preferably about 0.6 mils. Outer cover 10 can also be a meltblown or film material made of polyethylene, polypropylene or polyolefin copolymers such as ethylene vinyl acetate, ethylene methyl acrylate, ethylene ethyl acrylate, polyvinyl chloride, Nylon and the like. Other acceptable materials include a single spunbonded layer of the above types of materials, two layers of spunbonded and meltblown materials or a three-layer material of spunbonded, meltblown and spunbonded material. Suitable foam materials may also be used as outer cover 10 and include such foams as polyester, polyurethane, and EVA blended with polyester or polyurethane.

Outer cover 10 also has good hand properties.

Although FIGS. 1 and 2 illustrate composite 2 having elastomeric layer 6 between liner 4 and absorbent medium 8, the two can be interchanged such that absorbent medium 8 is adjacent liner 4 and elastomeric layer 6 is adjacent cover 10.

Figure 3:
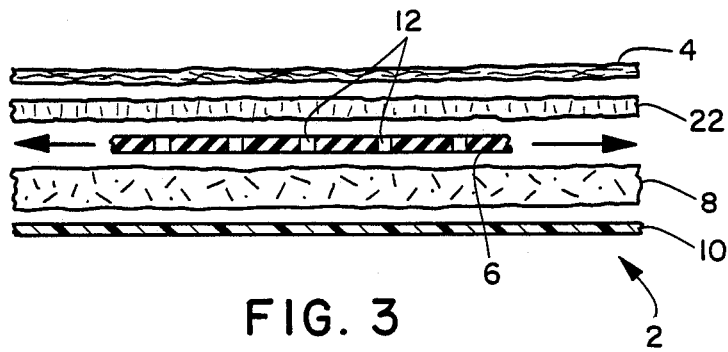
FIG. 3 illustrates another embodiment of the composite before the layers are joined together.
Figure 4:
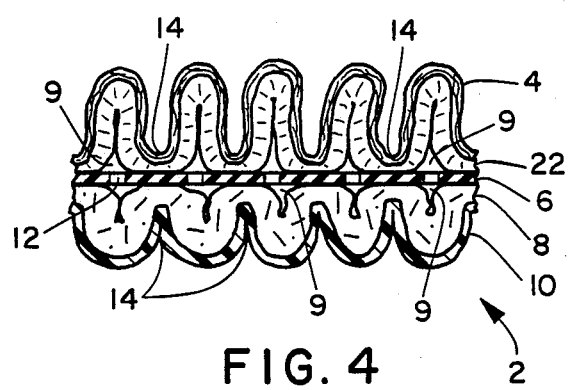
FIG. 4 is the embodiment in FIG. 3 after the layers have been joined together.

Referring now to FIGS. 3 and 4, another embodiment of stretchable absorbent composite 2 is illustrated wherein transfer layer 22 has been added between liner 4 and elastomeric layer 6. One of the purposes of transfer layer 22 is to provide rapid fluid transfer in the Z-direction, which is generally the direction perpendicular to the plane of stretchable absorbent composite 2. By thus providing rapid liquid transfer in the Z-direction, the absorbent rate of stretchable absorbent composite 2 is increased. Transfer layer 22 also preferably has low rewet properties and improved wet resiliency. One method of decreasing rewet properties is by distancing the liner from the absorbent, such as by means of air pockets 9. A method for increasing wet resiliency is the use of synthetic fibers or foams.

Rapid liquid transfer in the Z-direction, which can also be termed the vertical direction with reference to FIGS. 3 and 4, can be accomplished in one manner by orienting the fibers of transfer layer 22 in the Z-direction. This orientation can be accomplished by an air-laying process.

Transfer layer 22 is preferably a nonwoven web made of thermoplastic fibers, such as polyethylene, polypropylene, polyester and the like. Transfer layer 22 can be a bonded carded web, a meltblown web or a spunbond web of thermoplastic fibers or blends thereof. Specifically, transfer layer 22 can be a bonded carded web comprising 70 % by weight of polyester fibers and 30% by weight of a suitable binder, such as Chisso, low-melt powders, and the like, and having a basis weight of about 50 grams per square meter. A preferred basis weight range is about 30 to about 70 grams per square meter. Transfer layer 22 can also be a coform material, such as a carded web of polyester bonded to a spunbonded polypropylene carrier sheet and, if desired, a binding agent such as Chisso, low-melt powders, and the like. Specifically, a coform structure comprising 75% by weight polyester as a carded web bonded to a 25% by weight spunbonded polypropylene carrier sheet. The percentage weights of polyester and polypropylene can be varied as necessary or desired.

As with the embodiment of stretchable absorbent composite 2 in FIGS. 1 and 2, the embodiment illustrated in FIGS. 3 and 4 can have transfer layer 22, elastomeric layer 6 and absorbent medium 8 positioned in a different order than illustrated. Any order is acceptable as long as they are between liner 4 and outer cover 10. Preferably, the layers are positioned as illustrated in FIGS. 3 and 4.

Figure 6:
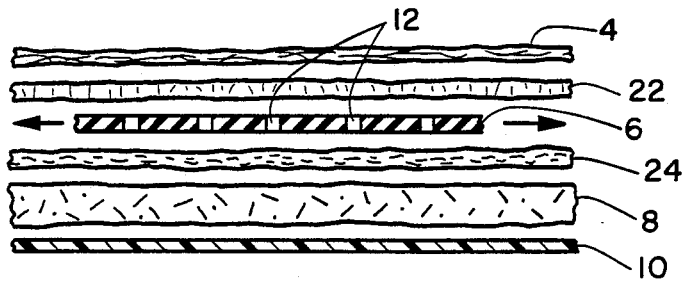
FIGS. 6 and 7 illustrate another embodiment of the composite before and after, respectively, the layers have been joined together.
Figure 7:
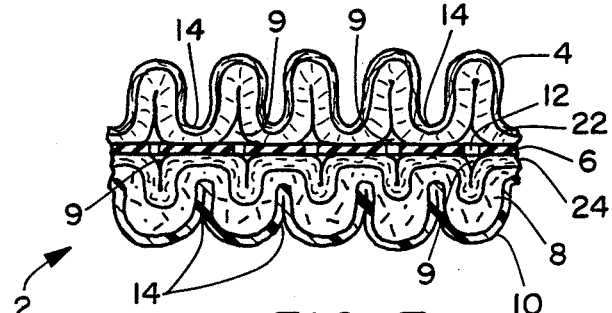

Referring now to FIGS. 6 and 7, another embodiment of stretchable absorbent composite 2 is illustrated wherein wicking layer 24 has been added between elastomeric layer 6 and absorbent medium 8. Wicking layer 24 serves to rapidly transfer liquid in the X- and Y-directions, which are in the plane of composite 2 so as to provide rapid absorption by absorbent medium 8. The rapid transfer of liquid in the X- and Y-direction is provided by orienting the fibers of wicking layer 24 in the horizontal direction, as viewed in FIGS. 6 and 7. In other words, the fibers in wicking layer 24 are generally perpendicular to the fibers in transfer layer 22. This horizontal or X- and Y-orientation of fibers can be attained by various processes, such as wet-laying and carding.

Wicking layer 24 can generally be made of the same type of materials as transfer layer 22.

Wicking layer 24, elastomeric layer 6, and absorbent 8 can be arranged in any order between liner 4 and outer cover 10. However, FIG. 6 illustrates the preferred order of liner 4, transfer layer 22, elastomeric layer 6, wicking layer 24, absorbent medium 8 and outer cover 10.

Figure 8:
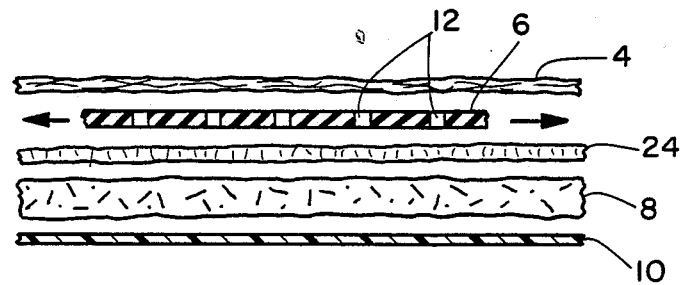
FIGS. 8 and 9 illustrate yet another embodiment of the composite before and after, respectively, the layers have been joined together.
Figure 9:
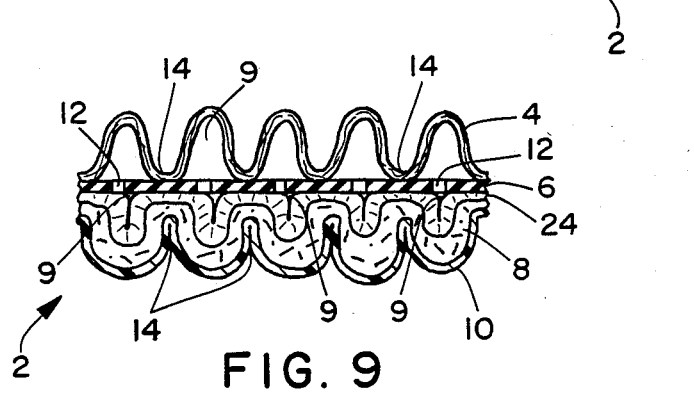
Figure 10:
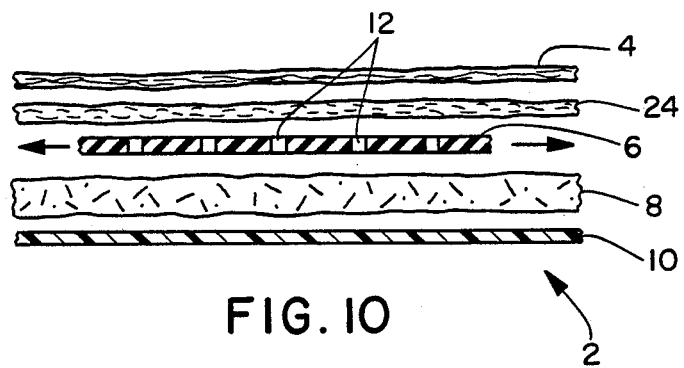
FIGS. 10 and 11 illustrate still another embodiment of the composite before and after, respectively, the layers have been joined together.
Figure 11:
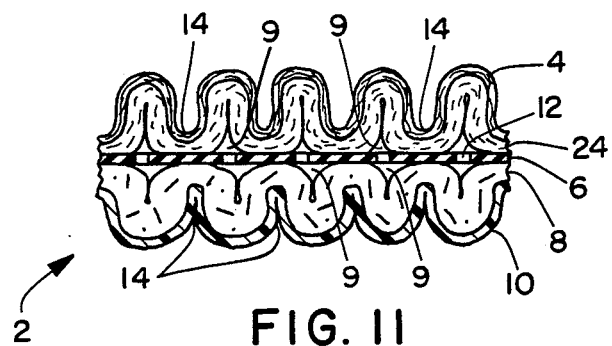

Referring now to FIG. 8 and 9, still another embodiment of stretchable absorbent composite 2 comprises liner 4, elastomeric layer 6, wicking layer 24, absorbent medium 8 and outer cover 10. Elastomeric layer 6 and wicking layer 24 can be interchanged in position between liner 4 and absorbent medium 8, as illustrated in FIGS. 10 and 11.

Figure 12:
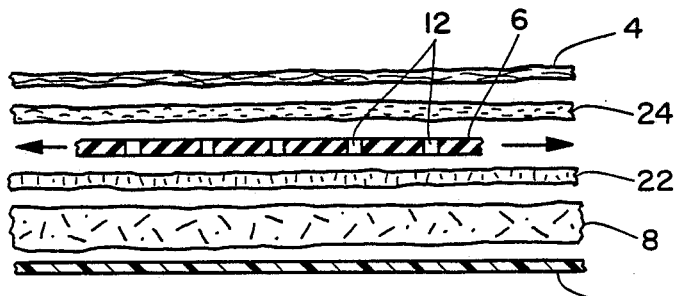
FIGS. 12 and 13 illustrate another embodiment of the composite before and after, respectively, the layers have been joined together.
Figure 13:
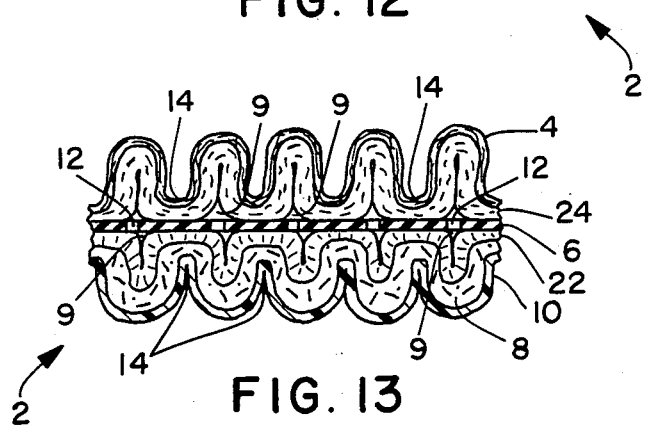

FIGS. 12 and 13 illustrate a variation on FIGS. 6 and 7, wherein layers 22, 24 are interchanged.

Because stretchable absorbent composite 2 contains thermoplastic components in its respective layers, it provides both a dry and wet integrity and resilience, both of which have functional and perceptual benefits. Furthermore, because of the bulking or gathering of resilient materials created by elastomeric layer 6, there is imparted to composite 2 the ability or capacity to maintain an original shape, which is a key factor in achieving superior containment.

Due to the intimate contact of the layers in composite 2 in combination with the overall bulking or gathering thereof, the absorbency characteristics of composite 2 are positively affected; for example, there is an increase in the rate of fluid transfer from the surface to the absorbent medium 8, and a minimizing of any wet collapse or clumping of cellulosic material should wood pulp fibers be a component of absorbent medium 8.

The use of transfer layer 22 and wicking layer 24 provides an increase in absorbent rates at the bond points and controlled flowback properties. A more detailed description of how the absorbent rates are increased at the bond points and the flowback properties minimized can be found in U.S. Pat. No. 4,397,644, filed Feb. 4, 1982, which is incorporated by reference herein.

Figure 14:
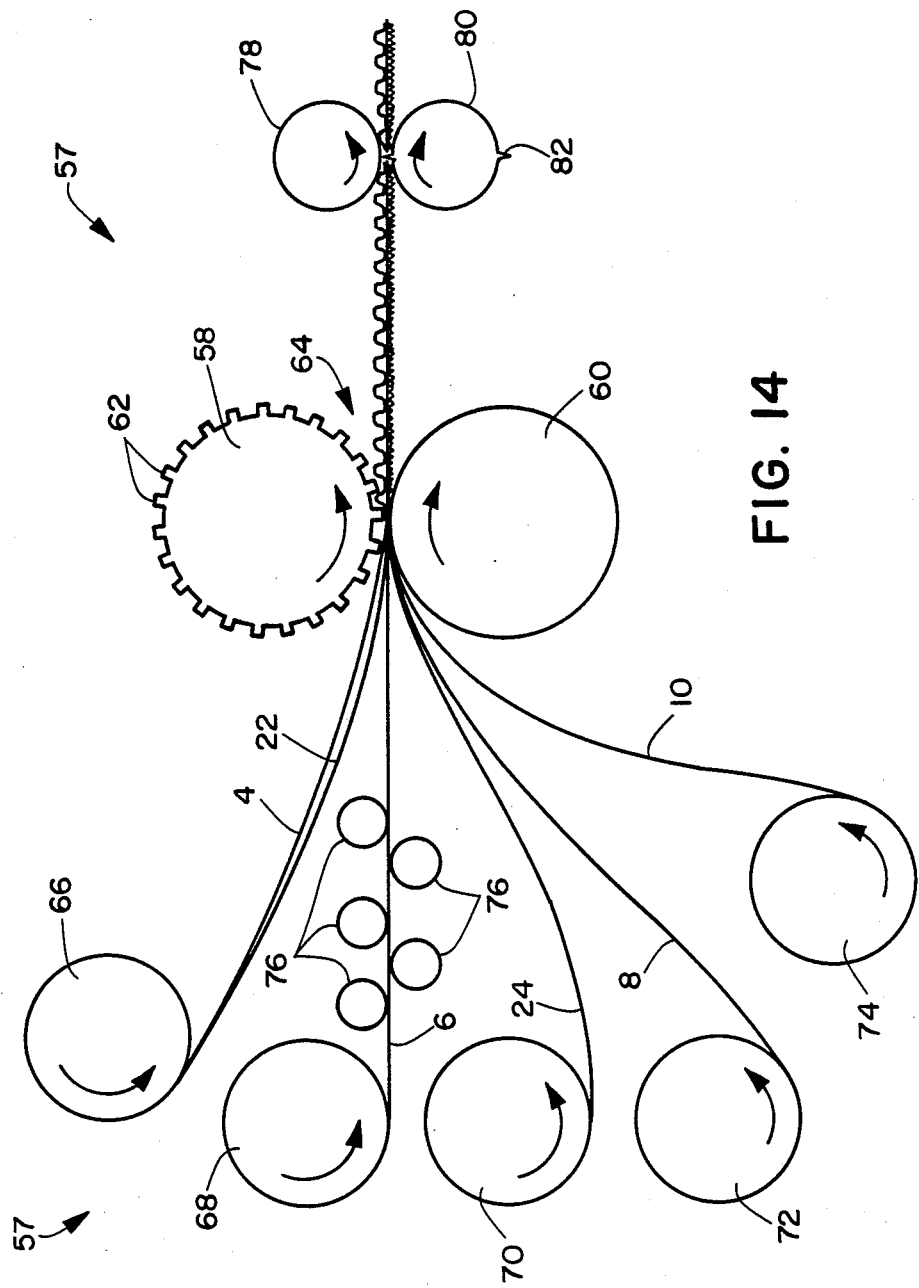
FIG. 14 is a schematic of an apparatus for making a stretchable absorbent composite.

Referring now to FIG. 14, apparatus 57 includes pattern roll 58 having a plurality of projections 62 selectively disposed thereon, and anvil 60 adjacent pattern roll 58 to form nip 64 therebetween. Both pattern roll 58 and anvil 60 are selectively rotatable in the direction of the arrows, and are selectively thermally controlled to provide a selected temperature on their respective outermost surfaces. Furthermore, either pattern roll 58 or anvil 60, or both, are moveable toward the other to vary selectively the pressure applied at nip 64. As mentioned earlier, projections 62 are selectively disposed on pattern roll 58 in any desired pattern, as further described below.

Apparatus 57 also comprises liner-transfer layer roll 66 that provides a two-layer web comprising liner 4 and transfer layer 22, which can be a coform material earlier described above and pre-formed separately on roll 66. Elastomeric layer roll 68 provides elastomeric layer 6, wicking layer roll 70 provides wicking layer 24, absorbent medium roll 72 provides absorbent medium 8 and outer cover roll 74 provides outer cover 10. The various roll supplies can be interchanged so as to vary the arrangement of the layers, as illustrated in FIGS. 1–13.

Figure 15:
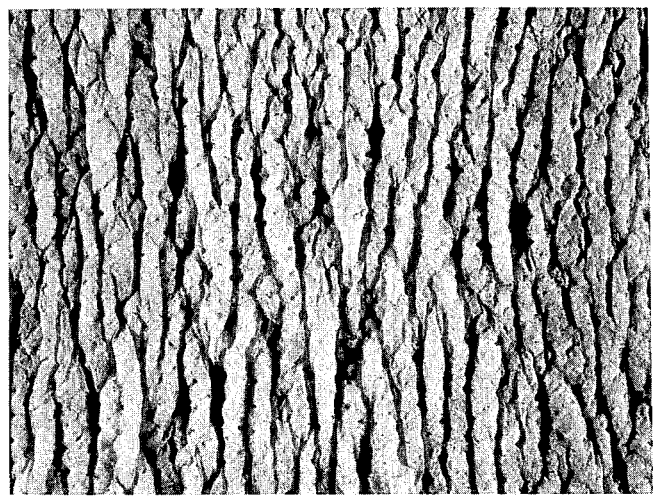
FIG. 15 is a photographic plan view of one side of a unidirectionally stretched composite.

In order to stretch elastomeric layer 6 before passing through nip 64, the rate of rotation of elastomeric layer roll 68 is selectively decreased below that of the selected rates of rotation of the other rolls 66, 70, 72 and 74. Because elastomeric roll 68 rotates at a slower speed, elastomeric layer 6 is stretched in the machine direction during its travel from roll 68 through nip 64. If desired, elastomeric layer 6 can also be stretched simultaneously, or only, in the cross-direction by use of stretching rolls 76 or any other known means, such as a tenter frame. Generally, stretching rolls 76 are curved or bowed so as to stretch elastomeric layer 6 in the cross-direction while being pulled thereacross. Control of the direction of stretch or elongation of elastomeric layer 6 is a useful feature not only in tailoring the properties and the shaping of the finished composite 2, but also in the handling and manipulating of composite 2 during the manufacturing processes. Naturally, the basis weight and stiffness of elastomeric layer 6 and the other selected layers, and the degree and direction of elongation of layer 6, may be selected to provide the desired properties in the finished composite 2. The stretching of elastomeric layer 6 in the machine direction only, or the cross-direction only, results in rows 16 of rugosities 14, as illustrated in FIGS. 5, 15, and 16. Similarly, the stretching or elongation of elastomeric layer 6 in both the machine and cross-direction results in the quilted configuration illustrated in FIGS. 5A, 17, and 18. If desired or necessary, one or all of rolls 76 can be provided with aperturing means, such as sharp or pointed projections, for aperturing elastomeric layer 6, whether it is being uni- or multi-directionally stretched.

As mentioned earlier, projections 62 can be selectively disposed on the outermost surface of pattern roll 58, and in doing so, allows the immobilization of selected areas of the stretchable absorbent composite 2 so as to control and vary the elastic properties. The immobilization effect can be controlled by either increasing or decreasing the number of bond points per unit area or the surface area of each individual bond point in a unit area.

As the bonded layers exit nip 64, they pass between anvil 78 and cutting roll 80, which has a plurality of blades 82 selectively disposed thereon. Blades 82 are selectively positioned to cut the bonded layers in any configuration.

Although pattern roll 58 with projections 62 is one method of bonding the layers together thermally, other bonding methods are contemplated by the method of the present invention and include ultrasonic bonding, adhesive bonding and other suitable bonding methods. Once the bonded layers pass through nip 64, the elastomeric layer is allowed to relax and to gather the other layers.

In a general embodiment of composite 2, there is a thermoplastic liner 4, thermoplastic transfer layer 22, thermoplastic elastomeric layer 6, thermoplastic wicking layer 24, thermoplastic absorbent medium 8 and thermoplastic outer cover 10. With this general embodiment, the temperature at which pattern roll 58 and anvil roll 60 are maintained falls within a range of 0° to about 400° F. The nip pressure at nip 64 is generally between 0 to about 1500 pounds per square inch, and the bond area, as a percentage of the total surface area, is between about 1 % to about 50%. The roll speed of pattern roll 58 and anvil 60 can also vary between 0 to about 1,000 feet per minute. As roll speed is increased or decreased, the required temperatures and pressures will also change as a function of the thermoplastic materials making up the various layers.

In a specific form, pattern roll 58 is maintained at a temperature between about 260° F. to about 330° F., and anvil 60 is maintained at a temperature between about 75° F. to about 210° F. The pressure at nip 64 is about 30 to about 80 p.s.i., the roll speed is about 15 to about 30 feet per minute, and the bond area is about 10% to about 20%. These particular parameters apply to a liner 4 made of spunbonded polypropylene having a basis weight of about 0.4 ounces per square yard; wicking layer 24 being a carded web of about 25% by weight polyester and 75% by weight polypropylene with a basis weight of about 50 grams per square meter; elastomeric layer 6 being made of Kraton G-2740X having a basis weight of about 70 grams per square meter; absorbent medium 8 being a mixture of about 75% by weight polyester and 25% by weight of binder and having mixed therewith a superabsorbent having a basis weight of about 16grams per square meter, the overall absorbent medium 8 having a basis weight of about 70 grams per square meter; and outer cover 10 being a film of polyester having a thickness of about 0.6 mils.

In another form, the temperature of pattern roll 58 is about 150° F. to about 250° F., and the temperature of anvil 60 is about 75° F. to about 210° F. The pressure at nip 64 is about 30 to about 80 p.s.i., the roll speed is about 15 to about 30 feet per minutes, and the bond area is about 10% to about 20%. These parameters apply to a composite 2 comprising a liner 4 of spunbonded polyethylene having a basis weight of about 0.4 ounces per square yard; wicking layer 24 being a carded web of about 70 % by weight polyester and 30% by weight of a suitable binder, having an overall basis weight of about 50 grams per square meter; elastomeric layer 6 being made of Kraton G-2740X having a basis weight of about 70grams per square meter; absorbent medium 8 being a web of about 60% by weight fluff pulp and 40% by weight of polyethylene and having mixed therewith a superabsorbent having a basis weight of about 16 grams per square meter, the overall basis weight of absorbent medium 8 being about 70 grams per square meter; and outer cover 10 being a polyethylene film having a thickness of about 0.6mils.

In another form, pattern roll 58 has a temperature of about 250° F. to about 310° F., and anvil 60 has a temperature of about 60° F. to about 90° F. The pressure at nip 64 is about 20 p.s.i. to about 40 p.s.i., the roll speeds about 10 to about 20 feet per minute, and the bond area between about 15% to about 25%. These parameters apply to a composite 2 comprising a liner 4 of spunbonded polypropylene having a basis weight of about 0.4ounces per square yard; a transfer layer 22 being a carded web of about 50% by weight polyester and about 50% by weight polypropylene and having a basis weight of about 30 grams per square meter; elastomeric layer 6 being made of Kraton G-2740X having a basis weight of about 70 grams per square meter; absorbent medium 8 being a web of about 60% by weight wood fluff pulp and about 40% by weight of polyethylene and having a superabsorbent mix therewith having a basis weight of about 16 grams per square meter, the overall basis weight of absorbent medium 8 being about 165 grams per square meter; and outer cover 10 being a polyethylene film having a thickness of about 0.6 mils.

While this invention has been described as having a preferred embodiment, it will be understood that it is capable of further modifications. This application is therefore intended to cover any variations, uses or adaptations of the invention following the general principles thereof, and including such departures from the present disclosure as come within known or customary practice in the art to which this invention pertains and fall within the limits of the appended claims.

What is claimed is:

1. An absorbent composite comprising:
   (a) a first layer;
   (b) a second layer;
   (c) an absorbent positioned between said first and second layers; and
   (d) an elastic layer positioned between said first layer and said absorbent, said elastic layer being resiliently stretchable in at least one direction from about 25% to 80% of an initial unstretched length with an elastic recovery of at least 10%, said elastic layer being bonded to both said first layer and said absorbent in at least a partially stretched condition wherein rugosities are formed in a substantial portion of both said absorbent and said first layer when said elastic layer is relaxed.

2. The composite of claim 1 wherein said first layer, said absorbent and said elastic layer are attached together at common bonding sites.

3. An absorbent composite comprising:
   a first layer having an outer surface and an inner surface;
   a second layer;
   an absorbent positioned between said first and second layers, said absorbent having first and second major surfaces one of which is attached to said inner surface of said first layer; and
   an elastic layer positioned between said inner surface of said first layer and said absorbent, said elastic being resiliently stretchable in at least one direction and attached in an elastically contractible condition to said inner surface of said first layer, said elastic layer extending over a substantial portion of said major surface of said absorbent and causing a plurality of rugosities to form in both said absorbent and said first layer when said elastic layer is in at least a partially relaxed condition whereby said rugosities render said absorbent elastically contractible to fit a range of user body sizes and assist in providing a dry surface adjacent to the user's skin.

4. The composite of claim 3 wherein said elastic layer has apertures formed therethrough which facilitate fluid transport from said first layer to said absorbent.

5. The article of claim 4 wherein said elastic layer is stretchable in a direction parallel to a longitudinal axis of said composite, thereby forming rows of rugosities in said composite which extend transversely to said longitudinal axis.

6. The composite of claim 5 wherein said elastic layer is stretchable in at least two directions resulting in a wormy and wrinkled pattern exhibited throughout said absorbent article when said elastic layer is at least partially relaxed.

7. The article of claim 6 wherein said elastic layer is stretchable in perpendicularly aligned directions.

8. The composite of claim 7 wherein one of said directions is along the longitudinal axis.

9. An absorbent composite comprising:
a first layer;
a second layer;
an absorbent positioned between said first and second layers;
an elastic layer disposed between said first layer and said absorbent, said elastic layer being resiliently stretchable in at least one direction and attached in at least a partially stretched condition to said first layer, said first layer being attached to said absorbent, said elastic layer causing a plurality of rugosities to be formed in both said absorbent and said first and second layers when said elastic layer is relaxed, rendering a substantial portion of said composite elastically contractible to fit a range of user body sizes while presenting a distinctively dry surface adapted for contact with the user's skin.

10. The composite of claim 9 wherein said elastic layer is positioned between said first layer and said absorbent, said elastic layer being apertured to facilitate fluid transport from said first layer to said absorbent.

11. The composite of claim 10 wherein said elastic layer is resiliently stretchable in a longitudinal direction thereby forming rows of rugosities which extend transversely to the longitudinal direction in said absorbent and said first and second layers.

12. The composite of claim 9 wherein said elastic layer is stretchable in at least two directions resulting in a wormy and wrinkled pattern exhibited throughout said absorbent article.

13. The composite of claim 12 wherein said elastic layer is stretchable in perpendicularly-aligned directions.

14. The composite of claim 13 wherein one of said directions is along the longitudinal axis.

15. The composite of claim 9 wherein said first layer comprises a liquid pervious bodyside cover wherein a plurality of rugosities are formed in said cover when said elastic layer is relaxed, presenting a wrinkled body-contacting surface having a distinctively soft and dry feel to the skin of the user.

16. The composite of claim 12 comprising a liquid transfer layer positioned between said elastic layer and said cover.

17. The composite of claim 16 wherein said elastic layer has an initial, unstretched length and is stretchable to more than about 25% of said initial length.

18. The composite of claim 17 wherein said elastic layer is stretchable from about 10% to 800% of said initial length.

19. The composite of claim 18 wherein said elastic layer has an elastic recovery of at least 10% of said stretched length.

20. The composite of claim 19 wherein said absorbent, said elastic layer, said second layer and said cover are attached together at common bonding sites.

21. An absorbent composite comprising:
a liquid pervious layer;
a liquid-impervious layer;
an absorbent positioned between said liquid pervious and impervious layers, said absorbent having first and second surfaces;
an elastic layer positioned between said liquid pervious layer and one of said first and second surfaces of said absorbent, said elastic layer being resiliently stretchable in at least one direction and attached to said liquid pervious layer and to said absorbent in a stretched condition, forming rugosities in said absorbent and said liquid pervious layer when said elastic layer is relaxed, thereby rendering a substantial portion of said absorbent elastically contractible to allow said article to fit a range of user body sizes.

22. The article of claim 21 wherein said elastic layer comprises a continuous sheet of material which is apertured.

23. The composite of claim 22 wherein said elastic sheet comprises a nonwoven web.

24. The composite of claim 23 wherein said elastic sheet, said absorbent and both said liquid pervious and liquid-impervious layers are attached together at common bond sites.

25. The composite of claim 21 wherein said elastic layer is resiliently stretchable from about 25% to 800% of an initial length and exhibits a recovery of at least 10% back to said initial length.

26. The composite of claim 25 wherein said elastic layer is stretchable in a longitudinal direction corresponding to the longitudinal axis of said composite, forming rows of rugosities which extend in an essentially transverse direction relative to the longitudinal axis when said elastic layer is relaxed.

27. The composite of claim 26 further comprising air pockets formed between adjacent rugosities when said article is in an at least partially relaxed condition.

28. The composite of claim 27 wherein said elastic layer is stretched in said transverse direction to form wrinkles in said absorbent and cause said liquid pervious layer to acquire a wormy appearance when said elastic layer is relaxed.

29. An absorbent composite comprising:
a liquid pervious cover;
a liquid-impervious baffle;
an absorbent positioned between said cover and baffle, said absorbent having first and second surfaces;
a liquid transfer layer positioned between said cover and said first surface of said absorbent for transferring liquid deposited on said cover generally in the Z directions toward said absorbent;
a wicking layer positioned between said second surface of said absorbent and said baffle for wicking liquid generally in the X- and Y-directions; and
an elastic layer positioned between said transfer layer and said first surface of said absorbent, said elastic layer being resiliently stretchable from about 25% to 800% of an initial length in a direction corresponding to the longitudinal axis of said composite wherein said elastic layer is attached in a stretched condition to said liquid transfer layer whereby rugosities are formed in said absorbent, said transfer layer and said elastic layer when said elastic layer is relaxed, rendering a substantial portion of said composite elastically contractible to fit a range of user body sizes.

30. The composite of claim 29 wherein said stretched elastic layer is bonded to said bodyside cover, said transfer layer, said wicking layer, said absorbent and said baffle at common bonding sites.

* * * * *

UNITED STATES PATENT AND TRADEMARK OFFICE
CERTIFICATE OF CORRECTION

PATENT NO. : 4,891,258
DATED : January 2, 1990
INVENTOR(S) : Anne M. Fahrenkrug

It is certified that error appears in the above-identified patent and that said Letters Patent is hereby corrected as shown below:

Column 10,
Line 24, delete "80%" and insert -- 800% --.

Signed and Sealed this

Twenty-fifth Day of June, 2002

Attest:

JAMES E. ROGAN
Attesting Officer  Director of the United States Patent and Trademark Office